United States Patent [19]

Spector et al.

[11] Patent Number: 5,072,733
[45] Date of Patent: Dec. 17, 1991

[54] SHOCK WAVE LITHOTRIPTER AND METHOD FOR USING THE SAME

[76] Inventors: Avner Spector; Sylvia Rutiser, both of 5-0 Metropolitan Ct., Gaithersburg, Md. 20878; Daniel Barnea, Tel Aviv, Israel

[21] Appl. No.: 493,398

[22] Filed: Mar. 14, 1990

[51] Int. Cl.$^5$ .............................................. A61B 17/22
[52] U.S. Cl. ............................ 128/660.03; 128/24 EL
[58] Field of Search ................... 128/24 E L, 660.03; 71/1 R

[56] References Cited

U.S. PATENT DOCUMENTS

| | | | |
|---|---|---|---|
| 4,669,483 | 6/1987 | Hepp et al. | 128/24 EL |
| 4,896,673 | 1/1990 | Rose et al. | 128/24 EL |
| 4,958,639 | 9/1990 | Uchiyama et al. | 128/660.03 |

FOREIGN PATENT DOCUMENTS 0316863  5/1989  European Pat. Off.

Primary Examiner—Ruth S. Smith
Attorney, Agent, or Firm—Sandler, Greenblum & Bernstein

[57] ABSTRACT

A shock wave lithotripter includes a shock wave generator for producing shock waves that are focused at a focus point remote from the shock wave generator during operation of the lithotripter, and an ultrasound probe having a transducer for producing ultrasound beams defining a plane of radiation during a calibration mode of operation of the lithotripter. Associated with the ultrasound probe is a screen for showing a display of the region illuminated by the beams. During calibration, the free end of a focal point target is positioned at the focus point of the lithotripter. The probe is moved in a direction perpendicular to the plane of the radiation beams produced by the probe until the free end of the target is illuminated by the ultrasound radiation. The location on the screen of the free end of the target is marked to indicate the location of the focus point of the shock wave generator in the display. The target is removed, and the lithotripter is then positioned relative to a patient such that a stone in the body of the patient, as displayed on the screen associated with the ultrasound scan, coincides with the mark on the screen representing the focus point of the lithotripter. Shock waves produced by the shock wave generator are thus focused on the stone which is fragmented by shock waves when the generator is activated.

13 Claims, 2 Drawing Sheets

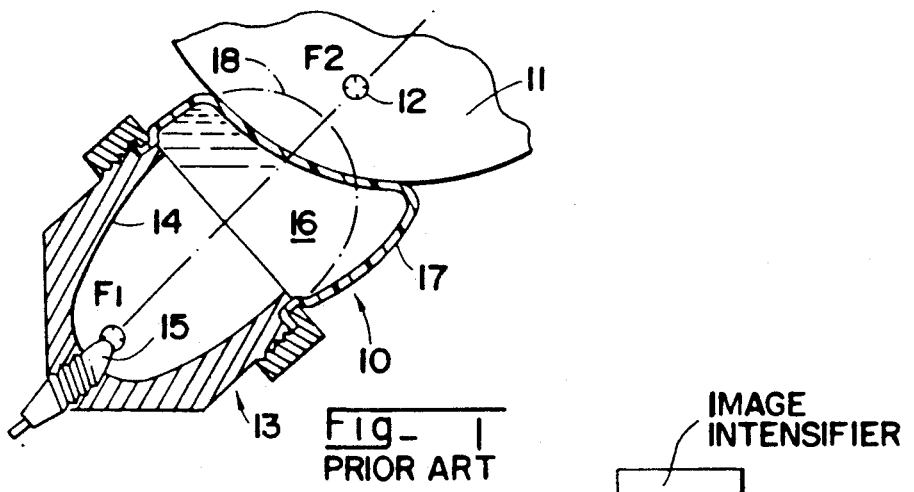
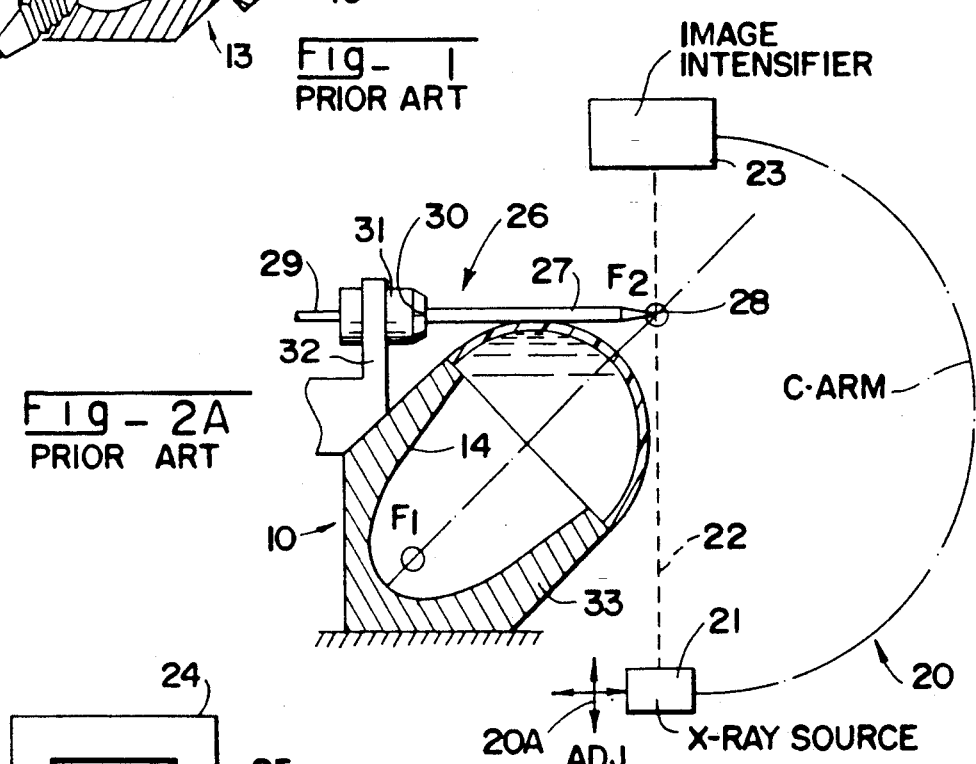
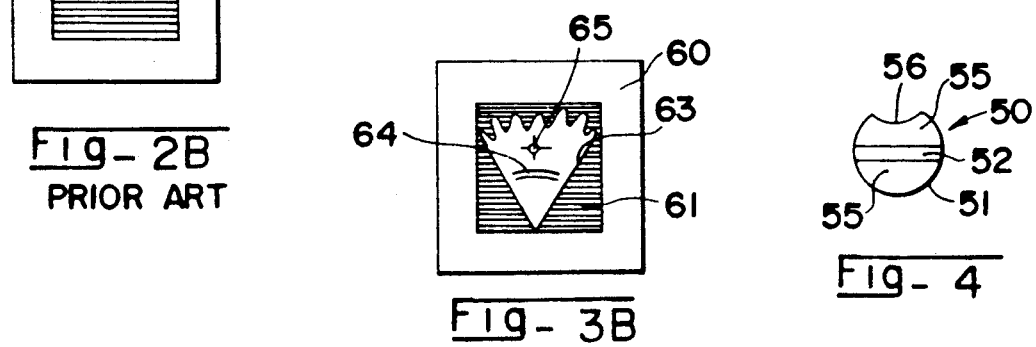
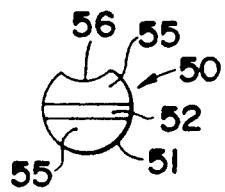

SHOCK WAVE LITHOTRIPTER AND METHOD FOR USING THE SAME

TECHNICAL FIELD

This invention relates to a shock wave lithotripter, and to a method for using the same.

BACKGROUND ART

Lithotripters are medical devices designed to fragment upper urinary tract stones, gall stones, renal calyceal stones, renal pelvic stones, and upper ureteral stones. Fragmentation of a stone in a patient is effected by focusing shock waves on the stones. Focusing is often achieved using an ellipsoidal reflector that is designed to reflect shock waves originating at one focus of the reflector to the other focus of the reflector which is coincident with the stone. Other types of focusing, such as a spherical array of piezoelectric transducers are also known.

A basic requirement in all types of lithotripters is to accurately position a patient relative to the lithotripter such that the stone to be fragmented is positioned precisely at the focus of the reflector. Mispositioning is physiologically damaging to the patient, and is to be avoided as much as possible. The problem, of course, is that the stone is internal to patients and its location cannot be determined by visual inspection. Thus, either X-ray based observations, in the case of kidney stones which are substantially opaque to X-ray radiation, or ultrasound scanning in the case of gall stones which are substantially transparent to X-ray radiation, must be used. When X-ray observation is employed, it is conventional to establish the location of a stone by using a fluoroscope in the form of a mobile C-arm carrying an X-ray source on one end of the arm and an image intensifier on the other end. The C-arm is physically associated with the lithotripter in that the focus of the reflector of the lithotripter has a fixed location in the display produced by the image intensifier. A patient is positioned on a treatment table between the X-ray source and the image intensifier. By viewing the stone in the display produced by the image intersifier, the table can be moved relative to the lithotripter until the stone is positioned in the display at a location coincident with the focus of the lithotripter reflector. After exact positioning is achieved, treatment by the lithotripter can be carried out.

In order to avoid intrusive imaging of a patient by X-rays, and especially in the case of treating gall stones which are transparent to X-rays, ultrasound imaging is currently being employed to locate a stone to be fragmented. The use of ultrasound for imaging purposes introduces a degree of complexity to the procedure described above because of the necessity for acoustically coupling the ultrasound transducer to the patient in order to achieve reasonable images, a complexity that is not present in X-ray imaging. While several techniques are presently available for using ultrasound imaging in a lithotripter environment, each technique has its unique deficiency. For example, one system in use utilizes an ultrasound transducer clamped in a fixed position relative to the shock wave generator means. This requires the transducer to be in direct contact with a patient during treatment to secure the required acoustical coupling with a patient. As a consequence, adjustment must be made for different patients because the depth of a stone in the body of the patient varies from patient.

In another system disclosed in U.S. Pat. No. 4,890,503, the ultrasound scanner is built into a spherical array of piezoelectric transducers with an ultrasound transducer being located at the center thereof. This permits a calibration process to be carried out prior to treatment wherein both the array of piezoelectric transducers and the ultrasound transducer are moved until the stone in a patient is located at the focus of the array. After this, the shockwave generator is activated.

One of the problems with this arrangement is the complexity of the equipment, and particularly maintenance or replacement of the ultrasound transducer which idles the equipment. In addition, this arrangement does not permit a technician to utilize the same ultrasound probe for both examination of the patient and for positioning the patient prior to and during treatment.

Other systems are known wherein an ultrasound transducer is located in a multi-jointed arm provided with position sensors at the joints by which the spatial location of the ultrasound transducer is determined. From such location, and with an ultrasound scan, the position in space of a stone in a patient is computed relative to the focus of the shock wave generator. The patient and/or generator are then manipulated so that the stone and focus coincide. Obviously, this is a very complicated system and, as a consequence, is very expensive.

It is therefore an object of the present invention to provide new and improved lithotripter, and a method for using the same, which is less complicated than the apparatus of the prior art, and which ameliorates the deficiencies therein.

BRIEF DESCRIPTION OF THE INVENTION

A shock wave lithotripter according to the present invention comprises shock wave generator means for producing shock waves that are focused at a focus point remote from the shock wave generating means during operation of the lithotripter, and an ultrasound probe having a transducer for producing ultrasound beams defining a plane of radiation during calibration of the lithotripter. Probe mounting means are provided for adjustably mounting the probe relative to the shock wave generator means, the mounting means being constructed and arranged so that the probe is spatially adjustable relative to the shock wave generator means during calibration of the lithotripter for effecting illumination by the ultrasound beams of a region containing the focus point.

Preferably, the shock wave generator means includes a flexible membrane containing coupling fluid through which shock waves propagate during operation of the lithotripter. The ultrasound transducer also engages the membrane for effecting propagation of the ultrasound beams through the coupling fluid during calibration.

In order to establish the location of the focus in a display produced by the ultrasound probe, the lithotripter includes a focal point target having a free end, and target mounting means for mounting the target relative to the shock wave generator means. In this way, the free end of the target is positionable at the focus point of the shock wave generator means. Display means including a screen are operatively associated with the ultrasound probe for displaying the plane illuminated by the ultrasound beams. Preferably, a flexible envelope on the focal point target surrounds the free end thereof, and coupling fluid is provided within the flexible envelope. Finally, the invention includes means for marking the screen with indicia representing the location of the free end cf said target.

A conventional ultrasound probe, for example, a sector scan probe, used for examination purposes, can be utilized in the shock wave lithotripter. When the probe is operated during calibration, adjustment to the probe mounting means is carried out until an image of the free end of the focal point target produced by the probe is displayed on the screen. The probe position is then fixed, and the location of the free end of the target is marked on the screen as a reference, and the calibration mode of the lithotripter is completed. During clinical use, the lithotripter is positioned in contact with a patient while the ultrasound scanner is operated. The patient and the lithotripter are moved relative to each other until a stone in the body of the patient is displayed on the screen in coincidence with the reference mark on the screen. The lithotripter can then be operated to produce shock waves that fragment the stone.

BRIEF DESCRIPTION OF THE DRAWINGS

Embodiments of the present invention are shown by way of example in the accompanying drawings wherein:

FIG. 1 is a sectional view through a conventional lithotripter having an elliptical reflector positioned relative to a patient such that the second focus of the lithotripter is coincident with a stone in the body of the patient;

FIG. 2A is a cross-section showing a conventional x-ray imaging system combined with a lithotripter, and to a tool for physically locating the second focal point of the elliptical reflector of the lithotripter;

FIG. 2B represents a fluoroscopic screen showing the location of the tool positioned at the second focal point of the ellipsoidal reflector of the lithotripter;

FIG. 3B is representative of the display produced by a sector scan ultrasound probe used in the apparatus of FIG. 3A;

FIG. 4 is an end view taken along the line 4-4 of FIG. 3A of the focal point target tool of the present invention.

DETAILED DESCRIPTION

Figure 3A:
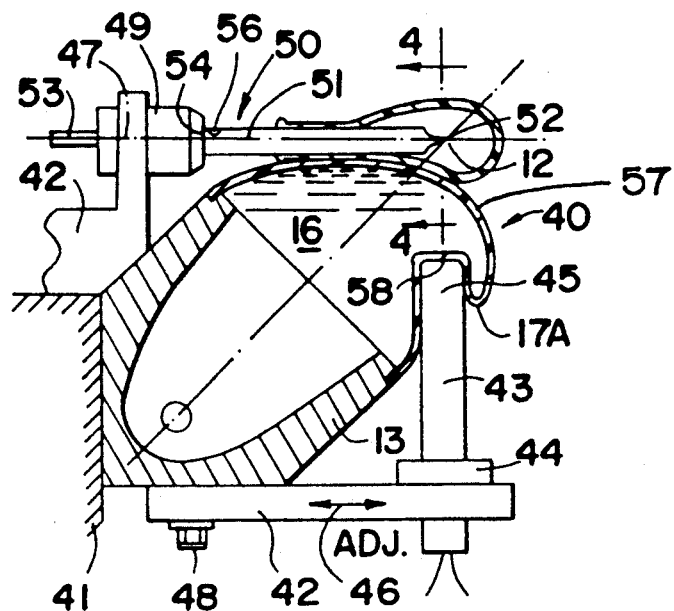
FIG. 3A is a cross-section of the present invention showing the technique by which the second focal point is detected using an ultrasonic scanner and a focal point target.
Figure 5:
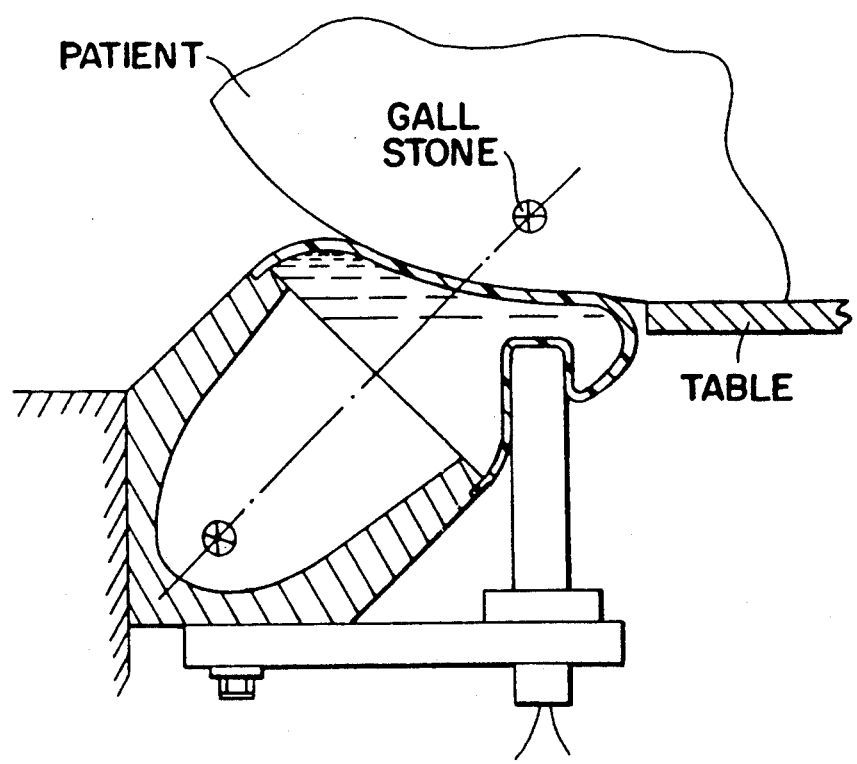
FIG. 5 is a schematic perspective view showing a lithotripter according to the present invention associated with a patient lying on a treatment table.

Referring now to FIG. 1 of the drawings, reference numeral 10 designates a conventional lithotripter operatively associated with patient 11 in preparation for fragmenting stone 12 located at focal point $F_2$ of shock wave generator 13. As shown, generator 13 has ellipsoidal reflector 14 at whose first focal point $F_1$ is transducer 15. The output of transducer 15 is coupled to patient 11 by coupling fluid 16 contained within flexible membrane 17 whose unstressed shape is indicated by chain-line 18. By suitable means, for example as described below, the patient is positioned relative to lithotripter 10 such that the location of stone 12 is coincident with focal point $F_2$ of the ellipsoidal reflector. In this position, the body of the patient will deform the membrane in the manner suggested in FIG. 1. A suitable acoustic gel is provided where membrane 17 contacts the patient to effect good acoustic coupling between generator 13 and patient 11. Actuation of transducer 15, which is a shock wave source, such as a spark plug, will produce a disturbance that propagates omnidirectionally from focal point $F_1$ throughout the coupling fluid; and the nature of ellipsoidal reflector 14 is such that all of the shock waves originating at point $F_1$ are focused by the reflector at point $F_2$ thereby fragmenting stone 12.

The problem, of course, is positioning the patient relative to the lithotripter so that the stone in the body of the patient is spatially positioned at remote focus $F_2$ of the ellipsoidal reflector. When X-rays are used to locate a stone in the body of a patient, a calibration procedure indicated by the arrangement shown in FIG. 2A may be employed. FIG. 2A shows lithotripter 10 operatively associated with C-arm mechanism 20 having X-ray source 21 located at one end of the C-arm for producing a conical beam of X-ray beams 22 that pass diametrically of the arm and that are incident on image intensifier 23 located on the other end of the arm. C-arm 20 is adjustable in both vertical and horizontal directions, as indicated schematically by arrows 20A, relative to reflector 14. This much of the lithotripter is conventional.

The object of the calibration procedure is to mark the location of focal point $F_2$ of the reflector on display 24 produced by image intensifier 23. Such location is indicated by reference numeral 25, and s determined by utilizing focal point target 26 which comprises elongated rod 27 having at one axial end, rounded point 28, and having at its other axial end reduced portion 29 defining shoulder 30 that seats against mounting hub 31 that is rigidly attached to mounting flange 32. The latter is rigidly attached to body 33 of lithotripter 10 which contains ellipsoidal reflector 14.

Rod 27 is slidably received in an axial bore (not shown) in hub 31 which is positioned, by reason of flange 32, in the vertical plane of symmetry of reflector 14. The length of the rod, and the position of shoulder 30 are selected such that when the shoulder abuts hub 31, point 28 of the rod is positioned precisely at focus $F_2$ of the reflector. Point 28 of the rod is imaged at different angular positions of the C-arm to determine the point in space corresponding to focus $F_2$. When this result is achieved, the screen of display 24 is marked as indicated at 25, and the spatial position of the C-arm is locked relative to the reflector. The calibration procedure is completed by removing target 26 from hub 31; and the apparatus is ready for clinical use in which a patient is placed on an adjustable table in a position where X-ray beams from source 21 will pass though the patient. Relative movement between the table and the lithotripter is effected until an image, on the screen of display 24, of a stone to be fragmented in the patient, is coincident with mark 25 on the screen. At this point, the stone to be fragmented will be located at focus $F_2$ of the lithotripter and clinical treatment can begin.

As indicated above, the use of X-rays in connection with clinical treatment of gall stones is inappropriate because such stones are transparent to X-rays. It is conventional, therefore, to use ultrasound imaging techniques to locate gall stones in a patient. Typically, a sector scan ultrasonic probe is used to examine patients, such a probe producing an essentially pencil beam of ultrasonic radiation that is oscillated through, typically, a 90° angle, to define a planar sector. Sector scans other than 90°, and ultrasound probes other than sector scan probes are also suitable for use in the present invention. For example, so-called linear probes, convex probes, or 3D probes can be used.

Conventional display apparatus associated with sector scan probe, indicated schematically in FIG. 3B by display 60 having screen 61, displays a sector shaped image 63 of a plane through a patient defined by the plane illuminated by the ultrasonic beam. Interfaces between different tissue in the plane illuminated by the ultrasonic beams in the patient produce echoes that appear as differences in brightness on the screen. Persons skilled in the art can interpret ultrasound images to identify gall stones, for example.

In order to position a lithotripter so that a gall stone of a patient is located at the remote focus $F_2$ of the reflector of the lithotripter, an ultrasound probe associated with the lithotripter is utilized. According to the present invention, the same probe used during examination of a patient, or optionally, a different but similar probe, can be used to properly position the patient relative to the lithotripter by following a calibration procedure illustrated schematically in FIG. 3A.

Shock wave generator 13 of lithotripter 40 shown in FIG. 3A is fixed to housing 41 and carries probe mounting arm 42 at its bottom, and mounting flange 42 at its top. Ultrasound probe 43 is attached by bracket 44 to the free end of mounting arm 42 which is located in the vertical plane of symmetry of the of reflector 14 thus positioning the probe in that plane. Bracket 44 is adjustable to effect vertical positioning of transducer 45 of the probe to a position spaced from focus point $F_2$ indicated by reference numeral 12. The spacing between the transducer of the probe and focus point $F_2$ is in accordance with the type of transducer utilized. In some sector scan probes, a space of 80-90 mm. is satisfactory, the spacing being chosen to be consistent with the probe such the the focus point is located within the field of view of the transducer.

The horizontal position of the probe on generator 13 is adjustable as indicated by arrows 46. Bolts 48 passing through arm 42 into generator 13 serve to secure the probe at a fixed horizontal displacement relative to focus $F_1$. As indicated below, the arm is clamped to generator 13 such that the plane of the sector scan of ultrasonic beams passes through remote focus $F_2$. That is to say, the plane of the sector scan is perpendicular to axis 51, and the apex of the scan lies in the vertical plane of symmetry of the reflector. The calibration procedure described below may be followed in order to properly position arm 42 on generator 13 so that the plane of the sector scan of the transducer passes through focus $F_2$.

In calibrating the apparatus of the present invention, focal point target 50 is utilized. Target 50, preferably aluminum, or other material that reflects ultrasound and is thus visible during ultrasound illumination. Preferably, the target is in the form of circular rod 51, terminates in free end 52. On the end of target 50 remote from end 52 is another rod 53 of reduced diameter thereby defining shoulder 54. Rod 53 is sized to be slidably received in a bore in hub 49 defining axis 47 which lies in the plane of vertical symmetry of the reflector. When rod 53 is in the bore, and shoulder 54 abuts hub 48, free end 52 of the target coincides with focus $F_2$.

As seen in FIG. 4, free end 52 of the target is in the form of a target surface defined by relief portions 55 adjacent to and symmetrically located on the free end. Such surface is substantially perpendicular to axis 47 of the target. Preferably, the surface is defined by a rectangle that is about 0.38 inches in width by about 0.05 inches thick. The elongated target surface will thus lie in the plane of the sector scan of the probe when arm 42 is properly adjusted. In order to so adjust the probe, the procedure described below is utilized.

Target 50 is provided with indicia 56 that is related to the orientation of the target surface on the free end of the target. In the example shown in FIG. 4, the indicia is in the form of a depression or notch located such that inspection of the notch reveals the angular position of the target surface. Indicia 56 is preferably located remotely from the target surface so that the indicia is visible when flexible membrane 57, filled with coupling fluid, is slipped over the free end of the target as shown in FIG. 3A. In this manner, a technician can tell by inspection of the angular position of the indicia on the target, the angular position of the target surface concealed by membrane 57.

Preferably, membrane 57 is filled with water, or the target may be encase in a phantom that simulates human tissue. For improved accuracy, the coupling fluid is chosen on the basis that the speed of sound therein approximates the speed of sound in tissue within the field of view of an ultrasound probe when it is used to image gall stones.

Free end 52 of the target may be displaced vertically relative to the actual physical focal point of the reflector to correct for differences in propagation (speed of sound) between the fluid filling the phantom and the human body. These differences are predictable and therefore can be accounted for either by displacing the alignment target from the actual focal point of the reflector, or by displacing the mark itself on the screen from the image of the target on the screen.

Finally, the present invention also includes membrane 17A which is similar to membrane 17 shown in FIG. 1. Preferably, membrane 17A is provided with pocket 58 which receives the free end of scanner 43. In such case, a suitable clamp (not shown) may be used to securely attach the membrane to the probe.

Prior to the calibration of apparatus 40, coupling fluid 16 is introduced into the space defined by the reflector of the lithotripter and membrane 17A, and conventional coupling gel is applied between membranes 17A and 57 where they engage to increase the acoustic coupling between the membranes. Probe 43 is then acutated causing the latter to produce sector scans passing through membranes 17A and 57. Experience shows that membrane 17A, because of its thickness, and to a lesser extent membrane 57, will be visible in the display as indicated by region 64 in FIG. 3B. The horizontal position of arm 42 is adjusted as a technician views screen 61 of the display apparatus associated with the probe. As the arm moves horizontally, the beams produced by the probe eventually will intersect the target surface on the free end of target 50. The result will be an elongated bright bar on the screen having a dimension elongated in the same direction as the target surface on target 50. A mark can be made on the screen itself with a suitable marking device coinciding with the bright bar that represents the target surface. Bolts 48 are then tightened to clamp arm 42 at the selected position at which the beam from the ultrasound transducer passes through focal point $F_2$ of the reflector. At this point, the technician can rotate target 50 through about 90° by inspection of indicia 56, and another bright bar will be produced on the screen perpendicular to the first mentioned bright bar. The intersection of these two bars, indicated by reference numeral 65 in FIG. 3B, defines the location of focal point $F_2$ on the screen.

Alternatively, if the display system associated with the probe admits of it, an electronic marker can be applied to the screen to mark the location of an image of the target surface. When this description speaks of marking the position of an image of the target on the screen, it should be understood that this phrase is intended to include placing a mark on the screen in coincidence with an image of the target, as well as placing a mark on the screen displaced from the location of an image of the target by an amount that compensates for the difference in the speed of sound in the medium surrounding the target as compared to the speed of sound in the body of a patient.

At this point, target 50 is removed from the apparatus, and a patient is positioned on a treatment table such that the region of the body of the patient containing a stone to be fragmented is in the vicinity of the spatial location of focus $F_2$. Probe 43 is again activated, and the patient and the apparatus are moved relative to each other until the stone is detected in screen 61 of the display. Relative movement is continued until the stone is located in coincidence with indicia 65 representing the location of focus $F_2$ of the reflector. When this is achieved, the technician may operate the lithotripter and cause fragmentation of the stone.

The advantages and improved results furnished by the method and apparatus of the present invention are apparent from the foregoing description of the preferred embodiment of the invention. Various changes and modifications may be made without departing from the spirit and scope of the invention as described in the appended claims.

What is claimed is:

1. A shock wave lithotripter comprising:
   a) shock wave generating means for producing shock waves that are focused at a focus point remote from said shock wave generating means during operation of said lithotripter;
   b) an ultrasound probe having a transducer for producing ultrasound beams defining a plane of radiation during calibration of said lithotripter;
   c) probe mounting means mounting said probe relative to said shock wave generating means;
   d) said mounting means being constructed and arranged to that the probe is spatially adjustable relative to said shock wave generating means during calibration and operation of said lithotripter for effecting illumination by said ultrasound beams of a region containing said focus point;
   e) a focal point target having a fee end;
   f) target mounting means mounting said target relative to said shock wave generating means such that said free end is positionable at said focus point; and
   g) display means having a screen for displaying the plane illuminated by said ultrasound beams such that said free end of said target is visible on said screen.

2. A shock wave lithotripter according to claim 1 wherein said shock wave generating means includes a membrane containing coupling fluid through which said shock waves propagate during operation of said lithotripter, said transducer engaging said membrane for effecting propagation of said ultrasound beams through said coupling fluid during calibration of said lithotripter.

3. A shock wave lithotripter according to claim 2 wherein said membrane includes a pocket for receiving said transducer.

4. A shock wave lithotripter according to claim 1 including a flexible envelope on said target surrounding the free end thereof, and coupling fluid in said flexible envelope.

5. A shock wave lithotripter according to claim 4 including means for marking on said screen a representation of the location of the free end of said target which is displayed on said screen when said probe is mounted at a predetermined location relative to said shock wave generating means.

6. A shock wave lithotripter according to claim 4 wherein said transducer is constructed and arranged to produce a sector scan, and said probe mounting means is constructed and arranged to effect positioning of said transducer at a location in which the free end of said target is illuminated by said sector scan.

7. A shock wave lithotripter according to claim 6 wherein the free end of said target has an elongated dimension, and the target has indicia for indicating when the angular position of the elongated direction is substantially perpendicular to the center line of said sector scan.

8. A shock wave lithotripter according to claim 6 wherein said probe mounting means is constructed and arranged so that said transducer is movable relative to said shock wave generating means in a direction perpendicular to said plane of radiation.

9. A shock wave lithotripter according to claim 8 including a coupling medium between said flexible envelope and said membrane.

10. A method for calibrating a lithotripter having shock wave generator means for producing shock waves that are focused at a focus point remote from said shock wave generator means during operation of said lithotripter, an ultrasound probe having a transducer for producing a sector scan of ultrasound radiation during calibration of said lithotripter, and a display for displaying an image produced by said sector scan, said method comprising the steps of:
   a) positioning the free end of a focal point target at said focus point;
   b) moving said probe in a direction perpendicular to said plane of said sector of radiation until said free end of said target is illuminated by said radiation;
   c) marking said display to indicate the locating of an image of the free end of said target; and
   d) removing the target and thereafter positioning the lithotripter relative to a patient such that a stone in the body of the patient detected by the ultrasound scan coincides with the marking on said display.

11. A method for utilizing a lithotripter having shock wave generator means for producing shock waves that are focused at a focus point remote from said shock wave generator means during operation of said lithotripter, an ultrasound probe having a transducer for producing a sector scan of ultrasound radiation during calibration of said lithotripter, and a display screen for displaying an image produced by said sector scan, said method comprising the steps of:
   a) positioning the free end of a focal point target at said focus point;

b) moving said probe in a direction perpendicular to said plane of said sector of radiation until said free end of said target is illuminated by said radiation;

c) marking said display to indicate the location of an image of the free end of said target;

d) removing the target and thereafter positioning the lithotripter relative to a patient such that a stone in the body of the patient detected by the ultrasound scan coincides with the marking on the display; and e) acoustically coupling the patient to the shock wave generator means and thereafter causing said shock wave generator means to produce shock waves that are focused on said stone.

12. A method according to claim 11 wherein said target has a longitudinal axis, and the free end of said target is elongated in a plane perpendicular to said axis, the marking step being carried out by marking the direction of elongation on the display of the image of the free end of said target at different angular positions of the target relative to its longitudinal axis.

13. A method according to claim 12 where the angular positions are about 90° apart.

* * * * *